(12) United States Patent
Öjelund

(10) Patent No.: US 10,172,573 B2
(45) Date of Patent: Jan. 8, 2019

(54) RADIOGRAPHIC SYSTEM AND METHOD FOR REDUCING MOTION BLUR AND SCATTER RADIATION

(71) Applicant: 3SHAPE A/S, Copenhagen K (DK)

(72) Inventor: Henrik Öjelund, Lyngby (DK)

(73) Assignee: 3SHAPE A/S, Copenhagen K (DK)

( * ) Notice: Subject to any disclaimer, the term of this patent is extended or adjusted under 35 U.S.C. 154(b) by 221 days.

(21) Appl. No.: 15/312,373

(22) PCT Filed: May 19, 2015

(86) PCT No.: PCT/EP2015/060984
§ 371 (c)(1),
(2) Date: Nov. 18, 2016

(87) PCT Pub. No.: WO2015/177140
PCT Pub. Date: Nov. 26, 2015

(65) Prior Publication Data
US 2017/0215821 A1   Aug. 3, 2017

(30) Foreign Application Priority Data

May 19, 2014   (DK) ................................ 2014 70293

(51) Int. Cl.
*A61B 6/00* (2006.01)
*A61B 6/06* (2006.01)
(Continued)

(52) U.S. Cl.
CPC ................ *A61B 6/06* (2013.01); *A61B 6/032* (2013.01); *A61B 6/4085* (2013.01);
(Continued)

(58) Field of Classification Search
CPC .......... A61B 6/032; A61B 6/06; A61B 6/405; A61B 6/4085; A61B 6/4208;
(Continued)

(56) References Cited

U.S. PATENT DOCUMENTS

| 4,143,273 A | 3/1979 | Richey et al. |
| 9,247,914 B2* | 2/2016 | Konno ................... A61B 6/032 |

(Continued)

FOREIGN PATENT DOCUMENTS

| EP | 1 046 903 A2 | 10/2000 |
| WO | WO 03/055393 A1 | 7/2003 |
| WO | WO 2005/009206 A2 | 2/2005 |
| WO | WO 2009/136400 A2 | 11/2009 |
| WO | WO 2013/132387 A2 | 9/2013 |

OTHER PUBLICATIONS

International Search Report (PCT/ISA/210) dated Jul. 23, 2015, by the European Patent Office as the International Searching Authority for International Application No. PCT/EP2015/060984.
(Continued)

*Primary Examiner* — Dani Fox
(74) *Attorney, Agent, or Firm* — Buchanan Ingersoll & Rooney P.C.

(57) ABSTRACT

A radiographic system including a radiation source emitting a radiation beam, a radiation sensor for detecting incident radiation from the radiation beam on a sensor area, at least one collimator arranged between the radiation source and the radiation sensor for masking the radiation beam to irradiate a radiation area on the sensor which is smaller than the sensor area and means for moving the collimator across the radiation beam, whereby the radiation area is moved across the sensor area.

18 Claims, 3 Drawing Sheets

(51) Int. Cl.
*A61B 6/03* (2006.01)
*G21K 1/04* (2006.01)
*H04N 5/32* (2006.01)
*H04N 5/217* (2011.01)
*H04N 5/235* (2006.01)
*H04N 5/33* (2006.01)
*H04N 5/353* (2011.01)

(52) U.S. Cl.
CPC .......... *A61B 6/4208* (2013.01); *A61B 6/4233* (2013.01); *G21K 1/043* (2013.01); *H04N 5/217* (2013.01); *H04N 5/2353* (2013.01); *H04N 5/32* (2013.01); *H04N 5/33* (2013.01); *A61B 6/405* (2013.01); *H04N 5/3532* (2013.01)

(58) Field of Classification Search
CPC ...... A61B 6/4233; G21K 1/043; H04N 5/217; H04N 5/2353; H04N 5/32; H04N 5/33; H04N 5/3532
See application file for complete search history.

(56) References Cited

U.S. PATENT DOCUMENTS

| | | |
|---|---|---|
| 2004/0081274 A1 | 4/2004 | Kresse et al. |
| 2004/0120457 A1 | 6/2004 | Karellas et al. |
| 2009/0147911 A1 | 6/2009 | Joosten et al. |
| 2011/0019798 A1 | 1/2011 | Kang et al. |
| 2013/0281840 A1* | 10/2013 | Vaughan ............... A61B 6/0414 600/425 |
| 2013/0294569 A1 | 11/2013 | Yoshikawa et al. |
| 2015/0023466 A1* | 1/2015 | Melman ................... A61B 6/06 378/42 |

OTHER PUBLICATIONS

Written Opinion (PCT/ISA/237) dated Jul. 23, 2015, by the European Patent Office as the International Searching Authority for International Application No. PCT/EP2015/060984.

Danish Search Report dated Oct. 24, 2014, by the Danish Patent Office in corresponding Danish Patent Application No. PA 2014 70293.

* cited by examiner

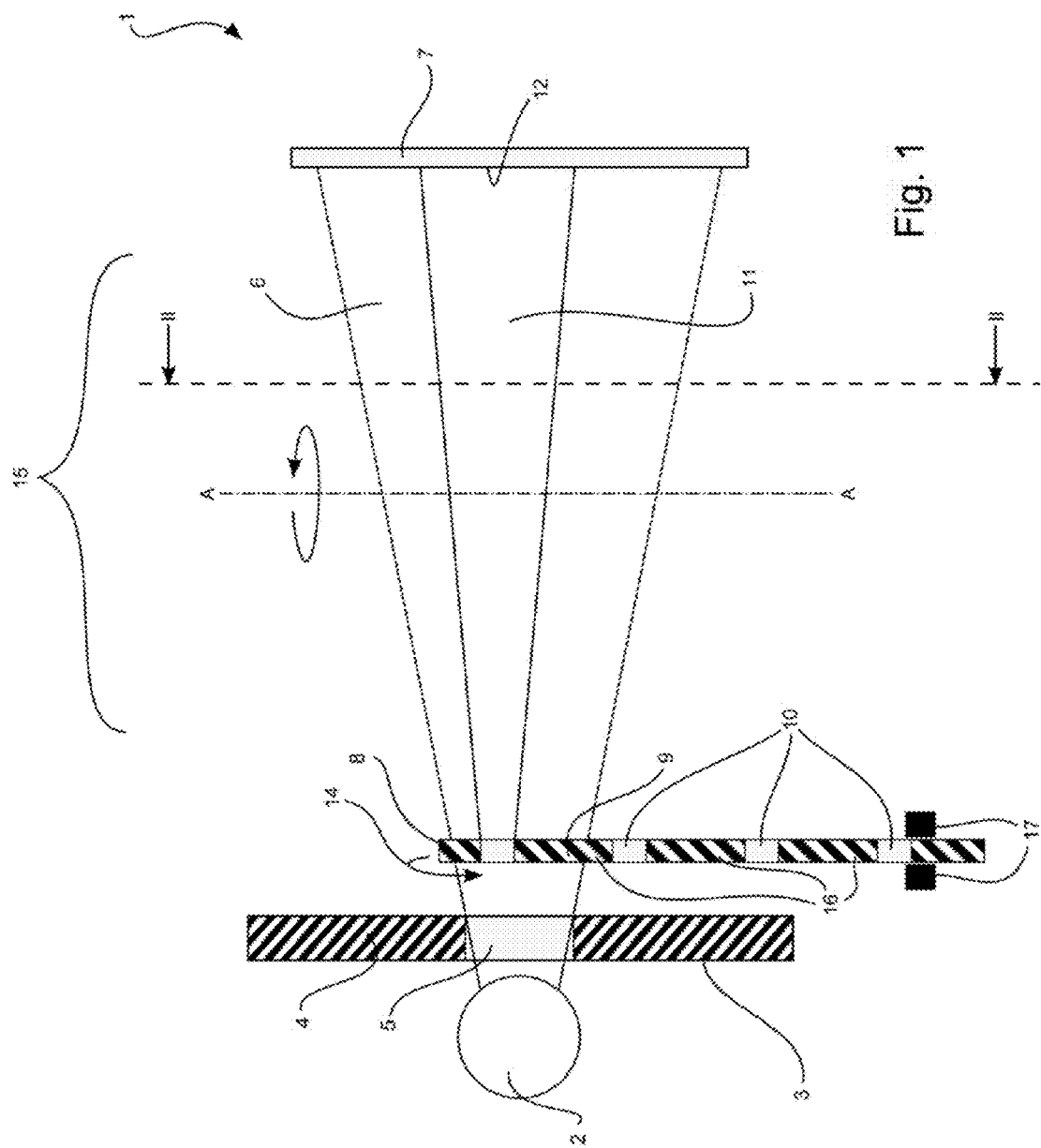

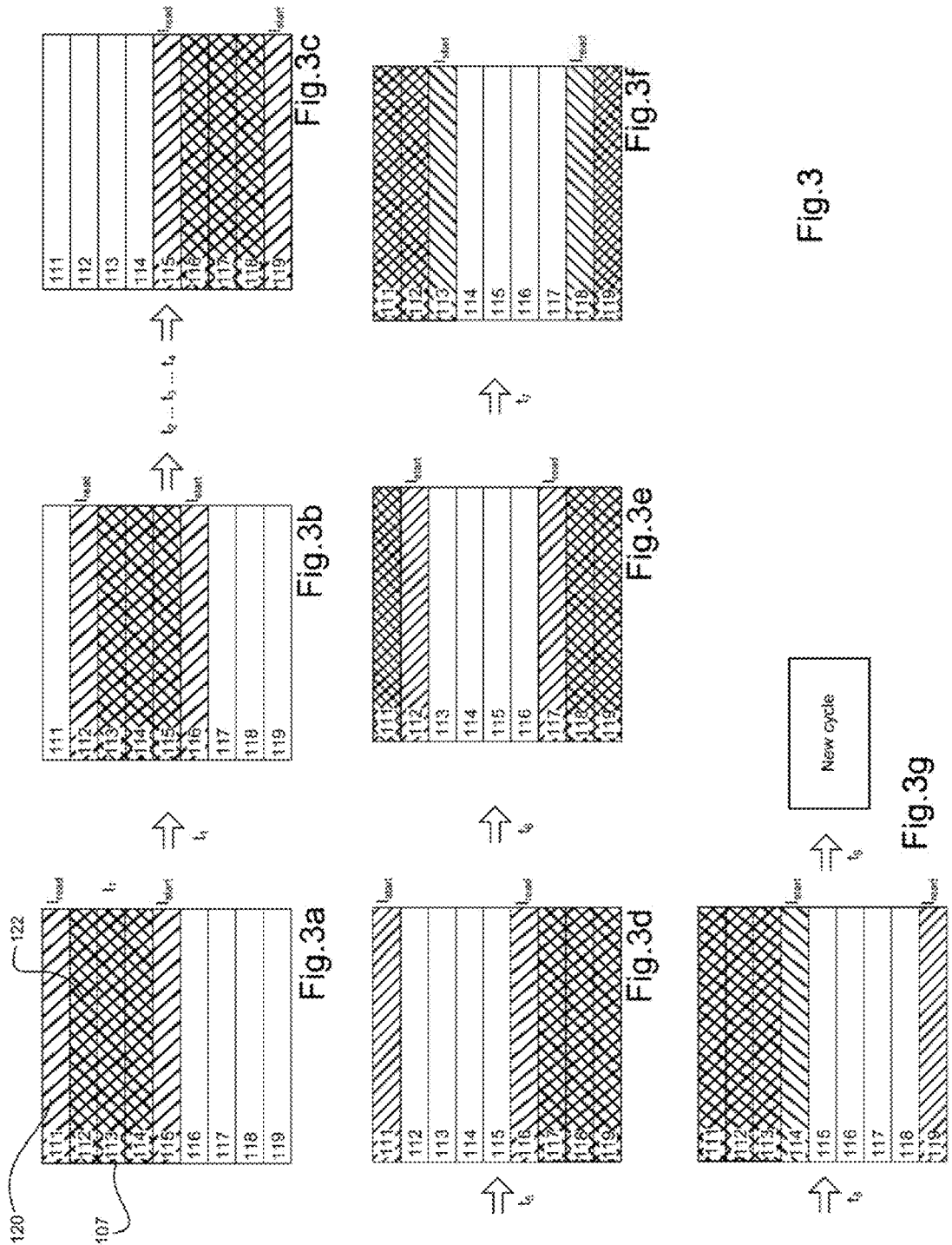

RADIOGRAPHIC SYSTEM AND METHOD FOR REDUCING MOTION BLUR AND SCATTER RADIATION

FIELD OF THE INVENTION

This invention generally relates to a radiographic system and a method for reducing motion blur and/or scatter radiation. More particularly, the invention relates to CBCT (Cone Beam Computed Tomography) scanners.

SUMMARY OF THE INVENTION

In one aspect there is disclosed a radiographic system comprising
- a radiation source emitting a radiation beam,
- a radiation sensor for detecting incident radiation from the radiation beam on a sensor area,
- at least one collimator arranged between the radiation source and the radiation sensor for masking the radiation beam to irradiate a radiation area on the sensor which is smaller than the sensor area, and
- means for moving the collimator across the radiation beam, whereby the radiation area is moved across the sensor area.

This provides a radiographic system wherein scatter radiation may be reduced, moreover if the system is moved during use the motion blur can also be reduced. This is particularly due to the small area of the radiation area compared to the sensor area as will be described in more detailed herein.

The radiation source can for example be a rotating anode tube, microfocus X-ray tubes and/or a Coolidge tube, which all are well known in the art and commonly used in radiographic systems.

In one embodiment a computer controlled device is connected to the radiation sensor, the device comprising software for reading the sensor output of the radiation area as the collimator is moved across the radiation beam.

By reading the sensor output continuously for a small area instead of the entire sensor motion blur can be further reduced.

In an alternative embodiment a computer controlled device is connected to the radiation sensor, the device software for reading the sensor output of the radiation area after the collimator is moved across the radiation beam.

A typical radiation sensor suitable for use in the radiographic system as disclosed herein is built up of rows. Each row is formed of a number of capacitors, where each capacitor accumulates an electric charge proportional to the radiation intensity in that area.

The rows are then read out to a computer for further processing. The rows can be exposed and subsequently read out all at once in a so-called global shutter type radiation sensor, or exposed and read out one at a time or in groups in a so-called rolling shutter type radiation sensor. Both types of sensors are well-known in the art.

For example, in one embodiment the sensor area comprises an active area where incident radiation is detected and an inactive area where incident radiation is not detected. This is typically done with a rolling shutter type (RST) radiation sensor.

As will be understood using a RST sensor is particularly advantageous. For example, using a RST sensor will result in an even image as the rows are read out continuously which reduces motion artifacts. Such motion artifacts are likely to occur if using a global type shutter where the whole sensor has to be read out each time the radiation area is read. Each read-out then have to be stitched together in a subsequent image processing step which results in an image that have jagged stitching areas where motion have occurred.

Additionally, by using a RST sensor the processing speed is increased since the time to read out the active area continuously of the RST sensor is much faster than having to read out the entire global sensor at each step and subsequent stitching the image together.

As described by Wikipedia:

"Rolling shutter is a method of image capture in which a still picture (in a still camera) or each frame of a video (in a video camera) is captured not by taking a snapshot of the entire scene at single instant in time but rather by scanning across the scene rapidly, either vertically or horizontally. In other words, not all parts of the image of the scene are recorded at exactly the same instant. (Though, during playback, the entire image of the scene is displayed at once, as if it represents a single instant in time.) This produces predictable distortions of fast-moving objects or rapid flashes of light. This is in contrast with "global shutter" in which the entire frame is captured at the same instant."

Accordingly, in one embodiment, the radiation sensor is a rolling shutter type sensor wherein at least two rows of the sensor are read out sequentially.

The advantage achieved by this is that undesired radiation, in particular scatter radiation, incident on the inactive area is not recorded by the sensor.

Scatter radiation occurs when an object or subject is radiated. Some of the radiation is reflected/scattered by the object. This radiation produces noise in the image and it is preferred that the registration thereof is avoided. In particular metal fillings create a lot of scatter and it can be very difficult to determine the exact shape of a filling in an x-ray if no attempt to reduce the scatter has been done.

In particular, a small active area results in a final radiographic image which is less influenced by scatter.

The active area is preferably larger than and/or overlaps the radiation area. This ensures that all the radiation received in the radiation area is detected. This is particularly advantageous as you want all the radiation emitted to be detected by the sensor. In most nations it is even a requirement in order for a device to be approved for sale that a patient is not exposed to radiation which is not recorded.

In order to ensure continuous overlap during operation the active area can be set to follow the radiation area as it is moved across the sensor area.

As disclosed above, the sensor can in one embodiment be a rolling shutter type (RST) sensor having an integration period defining the size of the active area of the sensor.

More specifically, the size of the active area may be determined by the number of active sensor rows active during the integration period.

For example, in order to detect incident radiation on a RST sensor the rows of capacitors forming the sensor has to be activated. This is referred to as integration start, $I_{start}$, which is the time at which a specific row is activated. From the integration start the capacitors of that specific row detects the incident radiation until the row is deactivated and the data from the row is read, which happens at integration read, $I_{read}$. The time period between $I_{start}$ and $I_{read}$ is referred to as the integration period, $I_T = I_{read} - I_{start}$.

During a set integration period a number of rows will thus be active and since the rows has a physical dimension the active area of the sensor will thus be: $A_{sensor} = W_{sensor} * (H_{row} * I_T / S_T)$, where $W_{sensor}$ is the width of the sensor or row, $H_{row}$ is the height of the row, $I_T$ is the integration period and $S_T$ is the sample period, i.e. the time it takes to read out a row and deactivate it.

The radiographic system disclosed herein is particularly advantageous when the radiographic system is a computational tomography (CT) scanner as the reduced radiation area allows for a faster exposure period of the radiation area from the sensor and thereby a reduced effect of motion blur/skew from the movement of the CT scanner.

For example, in order to compensate for motion blur the time at which the radiation area is read out is used in correlation with the position of the sensor configuration, i.e. the radiation source and radiation sensor, is moved. Accordingly, as the radiation area is moved across the sensor area and readout, as series of subsequent data sets are generated each having data representing the detected radiation for the radiation area and a time at which the radiation area was exposed. By knowing the exposure time and associate it with the movement of the sensor configuration in CT scanner, which also is known, it is possible to compensate for that movement in order to generate a radiographic image that have little or no motion blur.

In one embodiment as disclosed above it is thus the size and speed of the radiation area (and thus also the size and speed of the collimator moving across the radiation beam) that determines how long the sensor is exposed. Accordingly, by providing a narrower/smaller radiation area it is possible to reduce motion blur since a corresponding shorter motion has occurred in that time period.

Moreover, in embodiments where sensors with active and inactive areas are used, such as the RST sensor described herein, it is further possible to reduce the scatter effect.

Accordingly, by reducing motion blur and scatter effect sharper radiographic images can be generated.

In one embodiment the compensation of motion skew from the movement of the radiation source and the radiation sensor in the CT scanner is based on the time at which the collimator moves across the radiation beam.

In order to ensure that data is read out correctly from the radiation sensor it is important that the movement of the collimator and the operation of the radiation sensor are synchronized.

The timing of most common type radiation sensor can be very precisely controlled for the current application by the standard quartz crystal clock used with most computer controlled devices today.

However, the timing of the collimator and when the radiation area moves across the sensor area requires a separate device.

In one embodiment the timing of the collimator can be controlled by arranging a photo-sensor at the collimator. The photo-sensor comprises a light emitting source on one side of the collimator and a light detector on the other side of the collimator. As the collimator is moved an opening in the collimator passes the photo-sensor and thus allows the system to detect the movement of the collimator.

The collimator is advantageously designed so that it masks the radiation beam in cycles, such that the radiation area will move across the sensor area in at least two subsequent cycles, ie. two times in a row, wherein the movement direction, movement speed and the shape and size of the radiation area is the same in both cycles.

The collimator may in one embodiment comprise a series of openings or areas formed of a radiolucent or radio-transparent material separated by areas of radiopaque material. The width of each of the opening or areas are the same and chosen so that a desired radiation area is projected on the sensor. The width between each opening should correspond to the width of radiation beam at the collimators position. This provides a collimator setup wherein identical subsequent cycles as discussed can be provided. It should be understood that the widths referred to above are determined in the direction across the radiation sensor in which the collimator moves during operation.

As described previously the collimator is preferably synchronized with the radiation sensor in such a way that the passing of the opening of the through the radiation beam is timed with the read-out of the radiation sensor, such as the integration period of a rolling shutter type sensor.

The at least one collimator can be provided in a number of ways.

In one embodiment the at least one collimator comprises a disc formed of a radiopaque material with at least one radially extending opening or area formed of a radiolucent or radio-transparent material.

In another embodiment the at least one collimator comprises a wheel with a center axis arranged centered with the radiation source and wherein the rim of the wheel is formed of a radiopaque material and comprises at least one opening or area formed of a radiolucent or radio-transparent material.

The drive is preferably coupled to the wheel for rotating the wheel around its center.

Moreover, the least one opening or area formed of a radiolucent or radio-transparent material should advantageously extend parallel with the sensor area during rotation of the wheel.

In one embodiment the radiographic system comprises at least two collimators, wherein a first collimator is arranged as described previously and a second collimator arranged between the radiation source and the first collimator.

The second collimator comprises a second opening or second area formed of a radiolucent or radio-transparent material. The second collimator will typically be similar or correspond to collimators known to the person skilled in the art.

The first and second collimators are preferably both arranged opposite the radiation sensor relative to the scan volume. The scan volume is the area/volume where the object to be scanned is placed.

BRIEF DESCRIPTION OF THE DRAWINGS

The above and/or additional objects, features and advantages of the present invention, will be further described by the following illustrative and non-limiting detailed description of embodiments of the present invention, with reference to the appended drawings, wherein:

FIG. 1 shows a first embodiment of a radiographic system as disclosed herein,

FIG. 2b shows an enlarged area of the first embodiment of FIG. 2a, and

FIG. 3 illustrates in general the principles of the function of a radiographic system as disclosed herein.

DETAILED DESCRIPTION

Figure 2A:
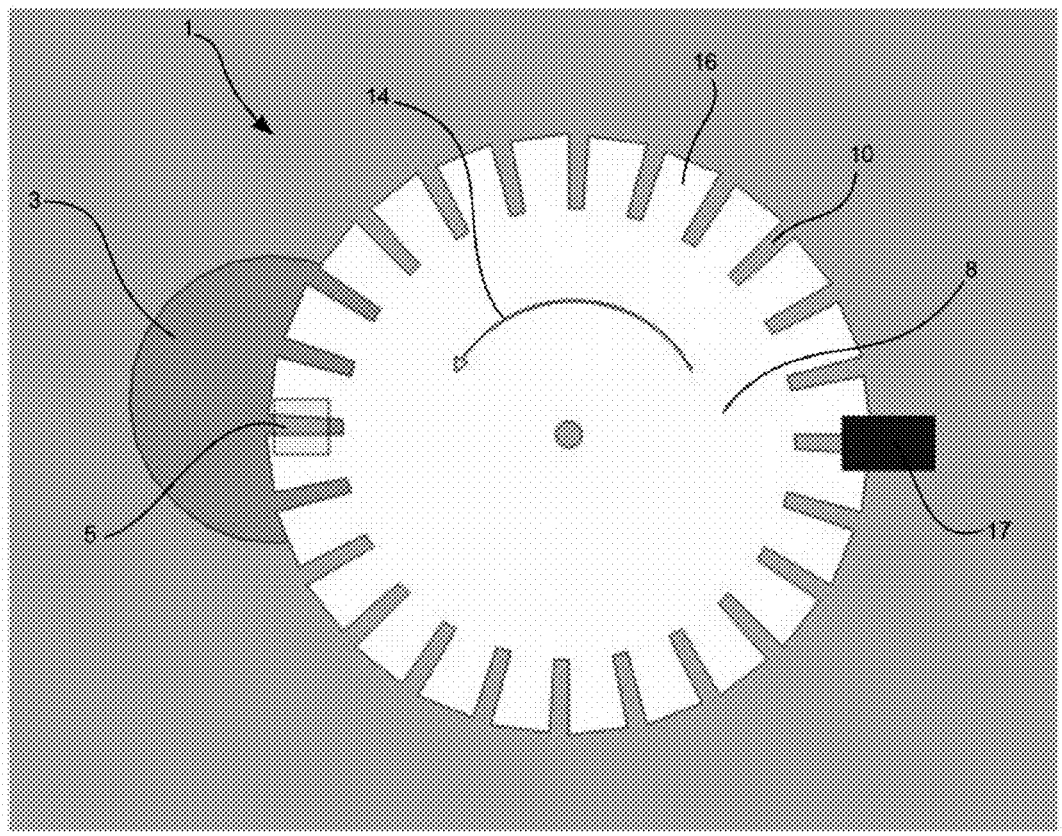
FIG. 2a shows the first embodiment of FIG. 1 along section II-II.
Figure 2B:
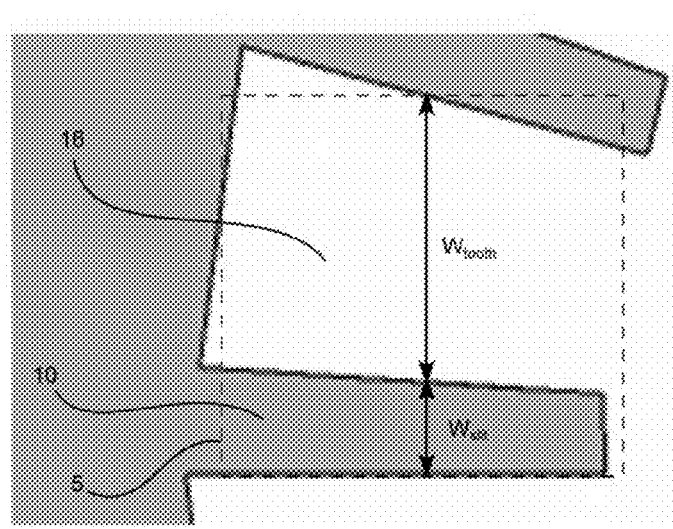

A first embodiment of a radiographic system 1 is illustrated in FIGS. 1, 2a and 2b. The radiographic systems is formed of a radiation source 2 and a standard collimator 3 formed of a radiopaque material 4 having an opening 5. The radiopaque material absorbs the radiation from the radiation source, thus, the collimator only allows radiation to pass through the opening 5, thereby generating a radiation beam 6.

A radiation sensor 7 is arranged opposite the radiation source. The radiation sensor is a rolling shutter type sensor. The distance to the radiation sensor and the size of the opening 5 in the standard collimator is dimensioned so that the expected incident radiation from the radiation beam 6 covers the surface of the radiation sensor.

A collimator disc 8 is placed between the standard collimator 3 and the radiation sensor 7. The collimator disc 8 is formed of a radiopaque material 9 and slits 10, the slits being separated by teeth 16. The collimator disc 8 provides a masked radiation beam 11, which irradiates a radiation area 12 on the radiation sensor that is smaller than the sensor area of the radiation sensor.

The slits 10 are provided as radial openings along the periphery of the disc. Each slit is identical in size and shape. A drive (not shown) is provided in order to rotate the disc 8 around its center axis 13 in an anti-clockwise direction as indicated by the arrow 14. As the collimator disc 8 is rotated the slits are moved across the radiation beam 6, thereby generating the masked radiation beam 11 which as a consequence of the motion generates the radiation area 12 which is moved across the sensor area of the radiation sensor 7. As can be understood each time a slit is moved across the radiation beam a cycle passes, and with the current setup it is possible to provide a masked radiation beam and thus also a radiation area that is identical in movement direction, movement speed, size and shape for each cycle.

During operation a subject such as the head of a patient (not shown) is placed in the scan volume 15 between the collimator disc and the radiation sensor. When the radiographic system is activated the radiographic system rotates around a rotation axis A-A extending through the scan volume while the radiation area repeatedly is moved across the sensor area.

To have an approximate constant flux of radiation the total width of the tooth and slit, $w_{total}=w_{slit}+w_{tooth}$, should approximate be equal to the height of the opening 5 in the standard collimator 3. The ratio between the slit width and the total width, $w_{slit}/w_{tooth}$, controls the effect of the wheel. A smaller ratio, $w_{slit}/w_{tooth} =>0$, decreases the scattering and motion blur but at the cost of increased load on the radiation source.

It is important to have a perfect synchronization with the radiation sensor to avoid unwanted radiation. For a rolling shutter type of sensor the number of integrating rows is calculated such that the active area of the radiation sensor always can encapsulate the radiation, i.e. the radiation area 12. For this a photo detector 17 is provided on the collimator disc which registers when slits and teeth pass. The synchronization can be achieved by first starting the radiation sensor and then adjusting the wheel speed such that photo detector signal is phase locked to the radiation sensors new frame signal. A constant phase delay has to be added to the photo detector signal for correcting for the relative position between the photo detector and the collimator.

The principle of the radiographic system and the method is schematically described in FIG. 3 which shows a sequence of radiographic sensor 7 registration 3a-3g, illustrating a full cycle.

FIG. 3 illustrates a radiation sensor 107 of a rolling shutter type similar to that described above with respect to FIGS. 1 and 2. The sensor has nine rows 111-119, where each row comprises capacitors for detecting radiation. The current embodiment of nine rows is for illustration purposes and it should be understood that in actual sensor the number of rows are typically much higher, such as 100 or 1000.

A row can either be active, wherein incident radiation is detected and an electric charge representative of the amount of radiation received while active is accumulated, or a row can be inactive wherein no radiation is detected.

In FIG. 3a the fifth row 115 activated at integration start, $I_{start}$ and the first row 111 is read and then deactivated (made inactive) at integration read. The time period between integration start and integration read is called the integration period $I_T$ and defines the active area 120, which in the FIG. 3a covers the first, second, third, fourth and fifth row 111, 112, 113, 114, 115.

However, in FIG. 3a direct radiation from the masked radiation beam is only received in the radiation area 122 which is in the second, third and fourth row. Scatter radiation may be received in the first and fifth row, which is unwanted. However, no radiation is received in rows six to nine 115, 116, 117, 118 and 119 as these are inactive. This is an advantage since any radiation incident on the inactive rows would be scatter radiation, which we want to avoid.

The active area 120 is slightly larger than the radiation area 122. This is in order to ensure that all the direct radiation incidents on the radiation are is received.

As described above the radiation sensor is synchronized with the motion of the collimator and thus the motion of the radiation area across the sensor. Accordingly, after a first time period $t_1$ the radiation area 122 now covers the third, fourth and fifth row and the sixth row is activated and the second row is read and subsequently deactivated. This sequence is followed at second $t_2$, third $t_3$ and fourth $t_4$ time periods until the integration start activates the ninth row 119, where the radiation area covers the sixth, seventh and eight row.

After the fifth time period $t_5$ the first row is activated in FIG. 3d in order to activate the upper row for a new pass of the radiation area. For example with the embodiment disclosed in FIG. 1-2 this is ensured by correct dimensioning of the width of the slits and the width of teeth of the collimator disc such that when the radiation area created by a slit passes the bottom of the radiation sensor, i.e. the ninth row 119, the radiation area created by a subsequent slit passes the top of the radiation sensor, i.e. the first row 111.

The current specific embodiment describes how it is possible to provide cycles of sensor registrations where the radiation area is identical for each cycle, both in movement, speed, size and shape. This has the advantage that rolling type sensors can be used in such a manner that the scanning speed is increased, while the radiation scatter and motion blur is reduced. The latter in particular when used in setups with rotating gantries, such as CT and CBCT scanners.

As understood and discussed previously a small radiation area 122 reduces motion blur since the radiographic system moves shorter (e.g. in the embodiment in FIGS. 1-2 the rotation around axis A-A is shorter) during the time a row is active than if the whole surface of the sensor was used to detect the radiation at once, i.e. the rows would be active for a longer time.

Moreover, interference from scatter radiation is reduced since rows which are not directly radiated are deactivated.

Embodiments:
1. A radiographic system comprising
   a radiation source emitting a radiation beam,
   a radiation sensor for detecting incident radiation from the radiation beam on a sensor area,
   at least one collimator arranged between the radiation source and the radiation sensor for masking the radiation beam to irradiate a radiation area on the sensor which is smaller than the sensor area, and means for moving the collimator across the radiation beam, whereby the radiation area is moved across the sensor area.

2. A radiographic system according to embodiment 1, further comprising a computer controlled device connected to the radiation sensor, the computer controlled device comprising software for reading the sensor output of the radiation area as the collimator is moved across the radiation beam.

3. A radiographic system according to embodiment 1 or 2, wherein the sensor area comprises an active area where incident radiation is detected and an inactive area where incident radiation is not detected.

4. A radiographic system according to embodiment 3, wherein the active area is larger than the radiation area.

5. A radiographic system according to embodiment 3 or 4, wherein the active area overlaps the radiation area.

6. A radiographic system according to embodiment 3, 4 or 5, wherein the active area follow the radiation area as it is moved across the sensor area.

7. A radiographic system according to embodiment 2, 3, 4, 5 or 6, wherein the sensor is a rolling shutter type sensor.

8. A radiographic system according to embodiment 7, wherein the rolling shutter type sensor comprises an integration period defining the size of the active area of the sensor.

9. A radiographic system according to embodiment 8, wherein the size of the active area is determined by the number of active sensor rows active during the integration period.

10. A radiographic system according to embodiment 7, 8 or 9, wherein the rolling shutter type sensor comprises wherein at least two rows of the sensor is read out sequentially.

11. A radiographic system according to any one of the embodiments 1-10, wherein the radiographic system is a computational tomography (CT) scanner.

12. A radiographic system according to embodiment 11, wherein compensation of motion skew from the movement of the radiation source and the radiation sensor in the CT scanner is based on the time at which the collimator moves across the radiation beam.

13. A radiographic system according to any one of the embodiment 1-12, wherein the collimator masks the radiation beam in cycles, such that the radiation area moves across the sensor area in at least two subsequent cycles during operation of the radiographic system.

14. A radiographic system according to embodiment 13, wherein the movement direction and movement speed of the radiation area across the sensor area is the same in the at least two cycles.

15. A radiographic system according to any one of the embodiments 1-14, wherein the at least one collimator comprises a disc formed of a radiopaque material with at least one radially extending opening or area formed of a radiolucent or radio-transparent material.

16. A radiographic system according to embodiment 15, wherein the disc plane and sensor plane are arranged parallel and a drive is coupled to the disc for rotating it around its center.

17. A radiographic system according to any one of the embodiments 1-16, wherein the at least one collimator comprises a wheel with a center axis arranged centered with the radiation source and wherein the rim of the wheel is formed of a radiopaque material and comprises at least one opening or area formed of a radiolucent or radio-transparent material.

18. A radiographic system according to embodiment 17, wherein a drive is coupled to the wheel for rotating the wheel around its center.

19. A radiographic system according to embodiment 17 or 18, wherein the least one opening or area formed of a radiolucent or radio-transparent material extends parallel with the sensor area during rotation of the wheel.

20. A radiographic system according to any one of the embodiments 1-19, wherein the system comprises at least two collimators, wherein a first collimator is arranged according to the at least one collimator of any one of the claims 1-19 and a second collimator arranged between the radiation source and the first collimator.

21. A radiographic system according to embodiment 20, wherein the second collimator comprises a second opening or second area formed of a radiolucent or radio-transparent material.

The invention claimed is:

1. A radiographic system comprising:
a radiation source emitting a radiation beam;
a radiation sensor for detecting incident radiation from the radiation beam on sensor area;
at least one collimator arranged between the radiation source and the radiation sensor for masking the radiation beam to irradiate a radiation area on the sensor which is smaller than the sensor area;
means for moving the collimator across the radiation beam, whereby the radiation area is moved across the sensor area;
wherein:
the sensor is a rolling shutter type sensor;
the radiographic system a computational tomography (CT) scanner; and
compensation of motion skew from the movement of the radiation source and the radiation sensor in the CT scanner is based on the time at which the collimator moves across the radiation beam.

2. A radiographic system according to claim 1, further comprising a computer controlled device connected to the radiation sensor, the computer controlled device comprising software for reading the sensor output of the radiation area as the collimator is moved across the radiation beam.

3. A radiographic system according to claim 1, wherein the sensor area comprises an active area where incident radiation is detected and inactive area where incident radiation is not detected.

4. A radiographic system according to claim 3, wherein the active area is larger than the radiation area.

5. A radiographic system according to claim 3, wherein the active area overlaps the radiation area.

6. A radiographic system according to claim 3, wherein the active area follows the radiation area as it is moved across the sensor area.

7. A radiographic system according to claim 1, wherein the rolling shutter type sensor comprises an integration period defining the size of the active area of the sensor.

8. A radiographic system according to claim 1, wherein the size of the active area is determined by the number of active sensor rows active during the integration period.

9. A radiographic system according to claim 1, wherein the rolling shutter type sensor comprises wherein at least two rows of the sensor is read out sequentially.

10. A radiographic system according to claim 1, wherein the collimator masks the radiation beam in cycles, such that the radiation area moves across the sensor area in at least two subsequent cycles during operation of the radiographic system.

11. A radiographic system according to claim 10, wherein the movement direction and movement speed of the radiation area across the sensor area is the same in the at least two cycles.

12. A radiographic system according to claim 1, wherein the at least one collimator comprises disc formed of a radiopaque material with at least one, radially extending opening or area formed of a radiolucent or radio-transparent material.

13. A radiographic system according to claim 12, wherein the disc plane and sensor plane are arranged parallel and a drive is coupled to the disc for rotating it around its center.

14. A radiographic system according to claim 1, wherein the at least one collimator comprises a wheel with a center axis arranged centered with the radiation source and wherein the rim of the wheel is formed of a radiopaque material and comprises at least one opening or area formed of a radiolucent or radio-transparent material.

15. A radiographic system according to claim 14, wherein a drive is coupled to the wheel for rotating the wheel around its center.

16. A radiographic system according to claim 14, wherein the least one opening or area formed of a radiolucent or radio-transparent material extends parallel with the sensor area during rotation of the wheel.

17. A radiographic system according to claim 1, wherein the system comprises at least two collimators, wherein:
   a first collimator is arranged between the radiation source and the radiation sensor for masking the radiation beam to irradiate a radiation area on the sensor which is smaller than the sensor area; and
   a second collimator arranged between the radiation source and the first collimator.

18. A radiographic system according to claim 17, wherein the second collimator comprises a second opening or second area formed of a radiolucent or radio-transparent material.

* * * * *